United States Patent [19]

Gils

[11] Patent Number: 4,481,291

[45] Date of Patent: Nov. 6, 1984

[54] PROCESS FOR DETERMINING STREPTOCOCCAL DESOXYRIBONUCLEASE B ACCORDING TO THE TOLUIDINE BLUE O METHOD

[75] Inventor: Reiner Gils, Wetter, Fed. Rep. of Germany

[73] Assignee: Behringwerke Aktiengesellschaft, Marburg an der Lahn, Fed. Rep. of Germany

[21] Appl. No.: 528,998

[22] Filed: Sep. 2, 1983

Related U.S. Application Data

[63] Continuation of Ser. No. 309,815, Oct. 8, 1981, abandoned.

[30] Foreign Application Priority Data

Oct. 10, 1980 [DE] Fed. Rep. of Germany ....... 3038286

[51] Int. Cl.$^3$ .......................... C12Q 1/68; C12Q 1/42; G01N 33/54
[52] U.S. Cl. ........................................... 435/6; 435/7; 435/21; 436/508
[58] Field of Search ................... 435/6, 7, 19, 21, 199; 424/2, 7; 436/63, 508

[56] References Cited

U.S. PATENT DOCUMENTS

| | | | |
|---|---|---|---|
| 3,906,120 | 9/1975 | Geating | 23/230 B |
| 3,990,946 | 11/1976 | Tiesler | 435/19 |
| 4,241,181 | 12/1980 | Lund | 435/36 |
| 4,307,189 | 12/1981 | Kit | 435/4 |

OTHER PUBLICATIONS

Douvas, "A method for Measuring the Number of Single and Double-Strand, Brakes introduced into DNA Molecules by the Action of DNase" Analytical Biochemistry 90 (1978) pp. 107-118.

The Merck Index, Stecher et al., ed. Merck & Co. Inc. Rahway, N.J. (1968) pp. 1057, and 1059.

*Primary Examiner*—Thomas G. Wiseman
*Assistant Examiner*—John E. Tarcza
*Attorney, Agent, or Firm*—Curtis, Morris & Safford

[57] ABSTRACT

A process is described for determining the desoxyribonuclease B and antibodies directed against desoxyribonuclease B. A toluidine blue O/DNA complex and a precipitating agent are used in this process.

6 Claims, No Drawings

PROCESS FOR DETERMINING STREPTOCOCCAL DESOXYRIBONUCLEASE B ACCORDING TO THE TOLUIDINE BLUE O METHOD

This application is a continuation of application Ser. No. 309,815, filed Oct. 8, 1981, now abandoned.

The invention relates to a process for determining desoxyribonuclease B and antibodies which are directed against desoxyribonuclease B, by means of a toluidine blue O/desoxyribonucleic acid complex.

Desoxyribonucleases (DNases) are extra-cellular metabolic products of streptococci of the group A according to Lancefield. Four DNases, which are designated by A, B, C and D, can be distinguished serologically and electrophoretically. These induce the formation of specific antibodies in humans. The determination of the DNase B antibodies has gained diagnostic importance for the recognition of streptococcal infections, since this enzyme is predominantly formed by streptococci of the group A.

In rheumatic fever produced by streptococci, an increase in anti-DNase B is also frequently found, in addition to an increase in the anti-streptolysin titer.

There is a good agreement, in most cases, between these values, and the anti-DNase B determination also offers a few additional diagnostic advantages. Especially in the case of skin infections, an increase in the anti-streptolysin content occurs very seldom, while a strong increase in the anti-DNase B titer is observed. There is therefore a need for the determination of the anti-streptococcal DNase B.

From German Patent Specification No. 2,344,441, a process for the determination of streptococcal desoxyribonuclease B is known, in which a complex of the metachromatic dye toluidine blue O and a desoxyribonucleic acid is used as the substrate. During the enzymatic degradation of this substrate, a flocculant precipitate of the dye is produced and the supernatant solution is decolorized.

A disadvantage of the process described is the long incubation time for the enzyme reaction.

A process, based on the toluidine blue O process, for the determination of streptococcal DNase B or its antibodies has now been found, the essential advantage of which process is the greater rapidity with which it can be carried out.

The subject of the invention is a process for determining DNase B by adding a DNA/toluidine blue O complex to a serial dilution of a solution of DNase B or of a solution of anti-DNase B to which a defined excess quantity of DNase B has previously been added, and determining the limiting concentration for precipitation, wherein a precipitating agent is added after the addition of the complex.

This precipitating agent is a base to which an amino acid and/or a salt is optionally added.

It has surprisingly been found that a visible precipitation of the free dye requires a longer time than the enzyme/substrate reaction, but the precipitation can be substantially accelerated by rendering the test mixture alkaline.

Inorganic bases are particularly suitable as the basic precipitating agent in the context of the invention, but organic bases can also be used.

From the group comprising the inorganic bases, aqueous solutions of alkaline earth metal hydroxides or alkali metal hydroxides, particularly calcium, potassium or sodium hydroxide solutions, are especially suitable owing to the simplicity with which they can be manipulated.

A precipitating agent with an amino acid or salt additive is preferred.

Glycine, β-alanine, leucine, sarcosine, alanine or glutamic acid are examples of suitable amino acids.

Sodium, potassium or magnesium chloride, potassium or magnesium sulfate, or, in general, chlorides and sulfates of alkali metals and alkaline earth metals are examples of suitable salts.

A mixture of the following constituents is particularly suitable as the precipitating agent according to the invention: 1 to 10%, preferably 5%, or a molar concentration, of an amino acid or a salt is added to a 0.5 to 5 molar, prefrably 2 to 4 molar, alkaline earth metal hydroxide or alkali metal hydroxide solution. The two components, or if appropriate also several components, are mixed in aqueous solution at 10° to 100° C., preferably at room temperature. A 0.5 to 5 molar basic solution, without the addition of an amino acid or a salt, can also be used as the precipitating agent; in this case, it is advisable to take a reading from the reaction no later than 30 minutes after the addition of the precipitating agent to the test mixture.

The following procedure can be followed for the preparation of a suitable precipitating agent: 10 to 100 grams of sodium chloride are added to 20 to 200 grams of sodium hydroxide in 1,000 ml of distilled water at 10° to 100° C., while stirring constantly. After the two components have completely dissolved, the solution is filtered.

The invention also relates to a process for precipitating the free dye after an incubation time of 20 to 60 minutes, preferably after 30 to 40 minutes, and subsequent warming of the test mixture for a short time to 40° to 70° C., preferably 50° to 60° C., for a period of 2 to 15 minutes, preferably 5 to 10 minutes, to aggregate the precipitates formed.

Owing to its simplicity, the process according to the invention is suitable for serial analyses.

Composing a so-called test kit, which is composed of the following reagents, is of advantage:

1. DNA/toluidine blue O substrate

The substrate is prepared according to known processes (German Patent Specification No. 2,344,441).

2. Streptococcal DNase B, for example an enzyme preparation from the culture filtrate of streptococci of the group A, prepared according to L. W. Wannamaker and W. Yasmineh, J. exp.Med. 126 (1967) 475. The addition of alkaline earth metal ions, preferably of Mg$^{++}$ ions, in 0.001 to 0.5 molar concentration, preferably 0.001 to 0.2 molar, for stabilizing the enzyme activity is advantageous. The solution is ready for use with an activity of approximately 30 U/ml according to Kunitz.

3. Imidazole buffer solution pH 7.8. The anti-DNase B Buffer is an imidazole buffer of pH 7.8 (17.0 g of imidazole/l), which contains 2.0 grams of bovine serum albumin, 1.47 gram of $CaCl_2 \times 2H_2O$ and 0.6 gram of $MgSO_4 \times 7H_2O$ per liter. The buffer solution, which additionally contains sodium azide (1.0 g/l), is used for preparing the serum dilution series.

4. Precipitating reagent comprising an aqueous hydroxide solution with an added stabilizer. In the preferred form, this is 2.5M NaOH (100 g/l) and 1M NaCl (58.5 g/l).

5. Anti-streptococcal DNase B Standard Serum is a human serum which has a defined concentration of antistreptococcal DNase B and which gives an anti-DNase B titer of 300 when the test is carried out as prescribed.

The process is preferably carried out as serial analyses, dilution series of the solutions in which the concentration of the anti-DNase B is to be determined being prepared. If serum is used, it is advantageous to warm this serum to about +56° C. for a short time. Non-specific reactions, which would falsify the measured result, are thereby eliminated. A known quantity of the DNase B solution is added to each dilution of the sample and is allowed to react with the anti-DNase B. DNA/toluidine blue substrate is thereafter added to the sample, only the DNase B not bonded by anti-DNase B being able to act on this substrate. During the enzymatic degradation of the DNA/toluidine blue O complex, the dye is liberated and is precipitated by the addition of the precipitating agent. The particular dilution series are compared with standard series of the anti-DNase B.

A MICRO-TITER plate is particularly suitable for carrying out the test, since, in addition to a series of sera, a standard series of the anti-DNase B, as well as appropriate controls for the enzyme and the substrate, can be applied adjacent to each other on the plate.

The following example illustrates the invention:

1. Preparation of the reagents:

1.1. The DNA/toluidine blue O substrate, lyophilized, is taken up in 5 ml of distilled water.
1.2. The streptococcal DNase, lyophilized, is taken up in 3 ml of distilled water.
1.3. The precipitating reagent (toluidine blue O precipitating agent) is an aqueous solution of 0.5 g of sodium hydroxide and 0.29 g of sodium chloride in 5 ml of water.
1.4. The anti-streptococcal DNase B Standard Serum is a liquid, stabilized human serum which has an anti-DNase B titer of 300 when the test is carried out as prescribed. The Standard Serum is ready for use.
1.5. The imidazole buffer solution, pH 7.8, is ready for use.

2. Preparation of the serum dilution series:

2.1. Each serum to be investigated is inactivated for 30 minutes in a water bath at +56° C.; a 1:50 dilution of the patient's serum is used for this purpose. Tube A: 0.1 ml of serum+4.9 ml of imidazole buffer solution, pH 7.8 (serum dilution 1:50)
2.2. After the inactivation, prepare a second serum dilution 1:75 from tube A. Tube B: 1.0 ml of serum dilution A+0.5 ml of imidazole buffer solution, pH 7.8 (serum dilution 1:75)
2.3. Also prepare dilution stages A (1:50) and B (1:75) from anti-DNase B Standard Serum, which does not need to be inactivated.
2.4. In a MICRO-TITER plate, prepare dilution series of standard and patient's sera of 1:50 to 1:2,400 with a volume of 25 μl.

3. Test mixture:

3.1. Introduce 25 μl of the ready-to-use streptococcal DNase B solution into each indentation, mix the solutions, close the plate and allow it to stand for 15 minutes at room temperature.
3.2. Using a micro-pipette, then introduce 50 μl of DNA/toluidine blue O substrate into all indentations, mix the solutions, close the plate and allow the mixtures to incubate for 30 minutes in an incubation apparatus at +37° C.
3.3 Introduce 25 μl of the basic precipitating agent into all indentations, mix the solutions well, close the plate and allow it to stand for 5-10 minutes at +56° C. in an incubating apparatus or water bath.

4. Evaluation:

In order to take a reading, the plate is placed on a milk glass disc, which can be illuminated from below, or on an anti-parallax mirror. The results can also be very well read off if the plate is held against a white surface. Those dilution stages in the standard and patient's sera are noted in which a reddish violet precipitation is not yet perceptible, and the anti-streptococcal DNase B concentration in the patient's serum is calculated therefrom:

Multiplication of the dilution factor of the patient's serum by the anti-DNase B concentration in the Standard Serum (titer stage 300), divided by the dilution factor in the Standard Serum.

For example Standard Serum: homogeneous reddish solution Indentation No. 5 (1:200)
Patient's serum: homogeneous reddish solution Indentation No. 7 (1:400) gives $$\frac{400 \times 300}{200} = 600 \text{ (titer)}$$

Compared to the conventional toluidine blue O process, a substantial saving in time and an improved readability can be achieved by means of the process according to the invention. The incubation time for the enzyme reaction is 4 hours in the conventional process and 30 minutes in the process according to the invention. If, in the case of the conventional process, there is no possibility of centrifuging, the plates have to be left to stand for a further 2 hours, as a rule, in order to improve the readability. This time during which the plates stand is also dispensed with in the new process. A total saving in time of approximately 5 hours can be achieved by the process according to the invention, and centrifuging the plates to obtain a better readability is also unnecessary.

I claim:

1. A process for determining desoxyribonuclease B, which comprises adding a DNA/toluidine blue O complex to a serial dilution of a solution of desoxyribonuclease B, or of a solution of anti-desoxyribonuclease B to which a defined excess quantity of desoxyribonuclease B has previously been added, introducing an amount of an agent sufficient to effect precipitation of toluidine blue O, said agent being both sodium hydroxide and sodium choride in solution or being both sodium hydroxide and glycine in solution, into said serial dilution and then incubating said serial dilution under conditions suitable for said precipitation of toluidine blue O to occur, measuring the lowest dilution at which precipitation occurs and correlating that with the amount of desoxyribonuclease B resulting in that precipitation.

2. A process as claimed in claim 1, wherein the precipitating agent is a solution of sodium hydroxide and glycine.

3. A process as claimed in claim 1, wherein the precipitating agent is a solution of sodium hydroxide and sodium chloride.

4. A process as claimed in claim 3, wherein the precipitating agent comprises a solution of from 2 to 20% sodium hydroxide and up to 10% of sodium chloride.

5. A process as claimed in claim 1, wherein the precipitating agent is introduced 15 to 60 minutes after the start of reaction between desoxyribonuclease B and the DNA/toluidine blue O complex, and wherein incubation is at a temperature of 40° to 70° C. for 2 to 15 minutes.

6. A process as claimed in claim 1, wherein the precipitating agent is introduced 30 minutes after the start of the reaction of desoxyribonuclease B and the DNA/toluidine blue O complex, and incubation is at a temperature of from 50° to 60° C. for 5 to 10 minutes.

* * * * *